United States Patent [19]

Hoffman et al.

[11] Patent Number: 5,440,058

[45] Date of Patent: Aug. 8, 1995

[54] METHOD FOR SEPARATING COMPOUNDS IN PROCESS STREAMS

[75] Inventors: William C. Hoffman, Dunbar; John P. Dever, Charleston, both of W. Va.

[73] Assignee: Union Carbide Chemicals & Plastics Technology Corporation, Danbury, Conn.

[21] Appl. No.: 255,338

[22] Filed: Jun. 7, 1994

[51] Int. Cl.⁶ .................. C07D 301/32; C07D 303/04; C07C 29/88; C07C 31/20
[52] U.S. Cl. .................. 549/538; 549/542; 568/872; 568/920
[58] Field of Search .............. 549/538, 542; 568/872, 568/920

[56] References Cited

U.S. PATENT DOCUMENTS

| | | | |
|---|---|---|---|
| 2,463,677 | 3/1949 | Brandner | 568/872 |
| 2,772,237 | 11/1956 | Bauman et al. | 568/872 |
| 2,868,832 | 1/1959 | Taylor et al. | 568/872 |
| 2,993,916 | 7/1961 | Normington | 549/542 |
| 3,213,113 | 10/1965 | Randall et al. | 549/542 |
| 3,816,478 | 6/1974 | Washall et al. | 549/542 |
| 3,904,656 | 9/1975 | Broz | 568/867 |
| 4,622,104 | 11/1986 | Néel et al. | 568/868 |
| 4,994,589 | 2/1991 | Notermann | 549/534 |

FOREIGN PATENT DOCUMENTS

| | | | |
|---|---|---|---|
| 667012 | 7/1963 | Canada | 549/542 |
| 694057 | 9/1964 | Canada | 549/542 |
| 9650 | 5/1969 | Japan | 549/542 |

*Primary Examiner*—Joseph E. Evans
*Attorney, Agent, or Firm*—J. B. Mauro

[57] ABSTRACT

A method, especially applicable on a continuous basis to commercial process streams, for treating unwanted by-products and/or impurities contained in those streams. The method comprises the reaction in situ of such by-products or impurities with a reagent, preferably selected for its reactivity under ambient conditions of the process stream, to produce one or more materials which may then be separated from the process by economical means. The treated stream may be recycled to the process for further processing. While the method is not limited as to the process to which it is applied nor to the reagent or reagents used, in one convenient embodiment, formaldehyde in aqueous solution is reacted with an alkali metal sulfite or bisulfite to produce the corresponding salt, which may then be separated essentially completely by, e.g., distillation or membrane separation, etc., or its concentration in the process may be controlled by, e.g., continuous removal of a purge stream, etc.

20 Claims, No Drawings

METHOD FOR SEPARATING COMPOUNDS IN PROCESS STREAMS

BACKGROUND OF THE INVENTION

1. Field of the Invention

This invention relates to methods for separating reactive, usually relatively volatile materials, typically present in relatively small concentrations, from process streams in which they are unwanted.

2. Discussion of the Prior Art

Chemical manufacturing processes frequently produce relatively minor amounts of what may be considered by-products or impurities, which are present in process streams and may result in a variety of problems ranging from UV absorption to discoloration to fouling of equipment. Formation of such materials is particularly troublesome in organic processes, where several materials may be produced as by-products which are difficult to separate from the desired products without expensive supplemental processing. A typical illustration is the unwanted production of carbonyl-containing compounds, which may lead to problems of corrosion, formation of color bodies, formation of polymeric contaminants, and the like. A specific case in point is the formation of aldehydes, including formaldehyde and higher molecular weight aldehydes, in the process for manufacturing alkylene oxides by the catalytic oxidation of alkenes.

Even though it is highly desirable to economize and simplify the relevant manufacturing processes, commercial processes nevertheless resort to complex and expensive distillation and comparable techniques to remove the unwanted materials. If such materials appear in the finished products, they must be either removed by costly post-manufacturing processing, or the products must be recycled or sold as off-specification or lower grade products. Moreover, such post-treatment procedures are undesirable because they may introduce different impurities into the product, which may have negative consequences in certain uses of the product. While various chemical reactions are known for the conversion of, e.g., formaldehyde to less volatile materials, no such reactions appear to have been heretofore incorporated directly into manufacturing processes. Accordingly, the present invention provides a technique of wide applicability whereby relatively volatile by-product materials are reacted in situ to form less volatile derivatives which can be readily separated by simple, relatively inexpensive means from the process streams in which they are found.

SUMMARY OF THE INVENTION

The present invention relates to a method for removing a reactive, usually relatively volatile, impurity in a process from a process stream, preferably an aqueous process stream, in which such impurity is dissolved, comprising:

(a) applying to said aqueous process stream a reactant under conditions under which said reactant reacts with said impurity to form a reaction product having a lower volatility than said impurity, and (b) removing at least a portion of said reaction product from the process.

The method of the invention is typically carried out by introducing a reagent external to the process stream being treated. By "external to the process stream being treated" is meant a reagent which does not occur naturally in that process stream, although it may occur naturally (or may be present as unreacted excess after treatment of the treated stream) in some other stream of the same process (or another process). In the former case, the reagent will be supplied from an external source; in the latter case, the reagent can be supplied by mixing at least part of the other stream containing it with the stream to be treated.

More particularly, in a process for making an alkylene oxide by the catalytic epoxidation of the corresponding alkene, the present invention relates to a method for separating formaldehyde by-product from at least some higher molecular weight aldehyde by-products and from the alkylene oxide in a process stream in which they are dissolved in water, comprising:

(a) mixing with said process stream a reactant which preferentially reacts with formaldehyde under the conditions of the process stream to form a reaction product or products having lower volatility than formaldehyde, and (b) removing at least a portion of said reaction product or products from the process.

Also, in a process for making alkylene oxide by the reaction of alkene and oxygen in which a stream containing alkene, oxygen, gas-phase inhibitor and at least one efficiency-enhancing gaseous member of a redox-half reaction pair is fed under alkylene oxide-producing conditions to a bed of catalyst comprising an impregnated silver metal on an inert, refractory solid support and an efficiency-enhancing amount of at least one efficiency-enhancing salt of a member of a redox-half reaction pair, a method for separating aldehyde, preferably formaldehyde, by-product from at least some higher molecular weight aldehyde by-products and from the alkylene oxide in a process stream in which they are dissolved in water, comprising:

(a) mixing with said process stream a reactant which preferentially reacts with formaldehyde and/or other aldehyde and/or one or more oxides of nitrogen, preferably under the ambient conditions of the process stream, to form one or more reaction product having lower volatility than the formaldehyde or other aldehyde or oxides of nitrogen, as the case may be, and (b) removing at least a portion of said reaction product or products from the process.

The method of the invention may use as reagents either oxidizing agents or reducing agents, as convenient for the process in question.

Removal of aldehydes from alkylene oxides and glycols has been specifically demonstrated herein using sodium bisulfite. The product of the reaction is a nonvolatile salt. However, prior art applications involved treating these aldehydes only in neat form, not as dilute aqueous solutions (see, e.g., U.S. Pat. Nos. 3,816,478 and 4,691,034, and Soviet Union 1,498,752).

DISCLOSURE OF THE INVENTION

Reactive, usually relatively volatile, organic or inorganic compounds formed as by-products in, or introduced into, manufacturing processes can be removed from process streams by conversion into relatively less volatile materials. While such removal can be batchwise, if desired, it is a particular advantage of the present method that removal can be continuous and can be fully integrated into the manufacturing process. In a particularly useful embodiment, such by-products in aqueous solution can be converted to nonvolatile salts in aqueous solution. The method of this invention can be applied to carbonyl-containing impurities, such as aldehydes and ketones, low molecular weight olefins, nitrogen-containing aromatic, aliphatic and inorganic compounds, e.g., oxides of nitrogen. Once the impurity is converted into a less volatile material, e.g., a nonvolatile salt, it may be removed by e.g., distillation or other suitable methods known in the art. Conversion into salts permits removal by distillation, extraction, membrane separation, or solid bed separation. In a preferred and very simple and economical embodiment, the converted by-product may be controlled by taking a purge stream off an appropriate process stream in which the material is present, e.g., a distillation column which separates the desired product(s) from unreacted materials and other materials to be recycled and/or further reacted.

As will be appreciated by those skilled in the art, the method of this invention is of broad utility and can be applied to any process having process streams containing unwanted, reactive materials which can be made to react with reagents which render such unwanted materials separable from the process. While the choice of such reagents will depend upon the material to be removed and the desired method of removal, it will be understood that use of such reagent should not result in the formation of further unwanted materials, nor cause other significant process difficulties. While the present method is desirably practiced under the ambient conditions of the process stream being treated, it will be appreciated that different conditions can also be used, as desired, by inclusion of appropriate heating, cooling, pressurization, and the like.

Processes where the method of this invention is particularly applicable include preparation of alkylene oxides and their derivatives, such as glycols, alkanolamines, polyalkylene oxides and other polymers. Reagents which can be used include alkali metal sulfites and bisulfites, peroxides, and potassium permanganate. Ammonium salts could also be used, provided that the presence of ammonia is not detrimental to the manufacturing process.

One of the preferred embodiments of the invention relates to known processes for the catalytic conversion of ethylene to ethylene oxide, with subsequent hydrolysis of the ethylene oxide to ethylene glycol. Such a process is well known and is described in general terms in various publications (e.g., *Kirk-Othmer Encyclopedia of Chemical Technology*, 4th Ed., vol. 9, pages 915–960 (John Wiley & Sons, New York, 1994)), and in numerous U.S. and non-U.S. patents. Numerous variations on such a process, principally concerned with the catalysis aspects, are also disclosed in the art. See, for example, U.S. Pat. No. 5,187,140 and U.S. patent application Ser. No. 08/091,352, filed Jul. 14, 1993, the disclosures of which are incorporated herein by reference.

One particularly effective process for the preparation of ethylene oxide utilizes silver catalysts of the type comprising at least one efficiency-enhancing salt of a member of a redox-half reaction pair which are employed in processes in which at least one efficiency-enhancing gaseous member of a redox-half reaction pair is present (described hereinbelow). The term "redox-half reaction" is defined herein to mean half-reactions like those found in equations presented in tables of standard reduction or oxidation potentials, also known as standard or single electrode potentials, of the type found in, for instance, *"Handbook of Chemistry"*, N. A. Lange, Editor, McGraw-Hill Book Company, Inc., pages 1213–1218 (1961) or *"CRC Handbook of Chemistry and Physics"*, 65th Edition, CRC Press, Inc., Boca Raton, Fla., pages D155–162 (1984). The term "redox-half reactions pair" refers to the pairs of atoms, molecules or ions or mixtures thereof which undergo oxidation or reduction in such half-reaction equations. Such terms as redox-half reaction pairs are used herein to include those members of the class of substances which provide the desired performance enhancement, rather than a mechanism of the chemistry occurring. Preferably, such compounds, when associated with the catalyst as salts of members of a half-reaction pair, are salts in which the anions are oxyanions, preferably an oxyanion of a polyvalent atom; that is, the atom of the anion to which oxygen is bonded is capable of existing, when bonded to a dissimilar atom, in different valence states. Potassium is the preferred cation, although sodium, rubidium and cesium may also be operable, and the preferred anions are nitrate, nitrite and other anions capable of undergoing displacement or other chemical reaction and forming nitrate anions under epoxidation conditions. Preferred salts include $KNO_3$ and $KNO_2$, with $KNO_3$ being most preferred.

The reaction conditions for carrying out the oxidation reaction are well-known and extensively described in the prior art. This applies to reaction conditions, such as temperature, pressure, residence time, concentration of reactants, gas-phase diluents (e.g., nitrogen, methane and $CO_2$), gas-phase inhibitors (e.g., ethylene chloride and ethylene dichloride), and the like.

The gases fed to the reactor may contain modifiers or inhibitors or additives such as disclosed by Law, et al., in U.S. Pat. Nos. 2,279,469 and 2,279,470, such as nitrogen oxides and nitrogen oxide generating compounds.

The terms "gaseous member of a redox-half reaction pair," "gaseous efficiency-enhancing member of a redox-half reaction pair," or like terms referred to herein, have a meaning similar to that for the "salt of a member of a redox-half reaction pair," or like terms, defined above. That is, these terms refer to members of half-reactions, represented in standard or single electrode potential tables in standard reference texts or handbooks which are in a gaseous state and are substances which, in the reaction equations represented in the texts, are either oxidized or reduced. The preferred gaseous efficiency-enhancing materials are compounds containing an element capable of existing in more than two valence states, preferably nitrogen and another element which is, preferably, oxygen. Examples of preferred gaseous efficiency-enhancing members of redox-half reaction pairs include at least one of $NO$, $NO_2$, $N_2O_4$, $N_2O_3$ or any gaseous substance capable of forming one of the aforementioned gases, particularly $NO$ and $NO_2$, under epoxidation conditions, and mixtures thereof with one or more of $PH_3$, $CO$, $SO_3$, $SO_2$, $P_2O_5$, and $P_2O_3$. $NO$ is often preferred as the gaseous efficiency-enhancing compound.

The desirability of recycling unreacted feed, or employing a single-pass system, or using successive reactions to increase conversion by employing reactors in a series arrangement can be readily determined by those skilled in the art. The particular mode of operation selected will usually be dictated by process economics.

Generally, the commercially-practiced processes for manufacturing ethylene oxide are carried out by continuously introducing a feed stream containing ethylene and oxygen to a catalyst-containing reactor at a temperature of from about 200° C. to 300° C., and a pressure which may vary from about five atmospheres to about 30 atmospheres depending upon the mass velocity and productivity desired. Residence times in large-scale reactors are generally on the order of about 0.1–5 seconds. Oxygen may be supplied to the reaction in an oxygen-containing stream, such as air or as commercial oxygen. The resulting ethylene oxide is separated and recovered from the reaction products using conventional methods.

To use a typical ethylene oxide manufacturing process as illustrative of the application of the invention, aldehydes may result from over-oxidation of the ethylene feed, air leaks into the system, and various other causes common in commercial-scale processes. Concentrations of such materials in aqueous streams may range from trace amounts to concentrations of 3000 ppm or more, depending upon the process stream in question. Such aqueous streams in typical commercial processes will be at temperatures ranging from about 35°–140 ° C. and at pH ranging from about 2–8. It will be readily understood by those skilled in the art that reagents useful in the method of this invention must be selected to be reactive under the conditions of use, but yet not so reactive as to cause unwanted side-reactions, nor the degradation of the reactants or products.

To discuss sodium bisulfite as a particularly useful reagent of the invention, its useful reactivity with formaldehyde will occur at temperatures ranging from about 0° to 100° C., or more, depending on pressure, with the preferred range being about 25° to 100° C.. Another important variable for the bisulfite reaction is the pH, which should be in the range of about 1 to 10, preferably about 5 to 8. The concentration of bisulfite used will, of course, depend upon the concentration of formaldehyde present in the system; however, the bisulfite should be present in at least a slight excess over the stoichiometric amount, in order to drive the equilibrium in favor of the desired reaction. Otherwise stated, the equivalence ratio of sodium bisulfite to formaldehyde should be at least slightly over 1:1. There is no theoretical upper limit to that ratio; however, there appears to be no practical benefit to a ratio over about 2:1. While the bisulfite will tend to react preferentially with formaldehyde, it will be understood that a ratio above about 2:1 will encourage the reaction to proceed also with acetaldehyde and optionally other aldehydes in the stream, depending upon the ratio and other reaction conditions chosen. This will be a desirable procedure where it is intended to effect separation by conversion of such heavier aldehydes.

As suggested above, the point (or points) of addition of a reagent of this invention is a matter of choice, depending upon the particular process being treated and its specific design; accordingly, it is not practical to give detailed advice. In general, however, it may be said that reagents capable of decomposition at high temperatures and/or pH levels should be introduced into the process at places where they will not encounter conditions which cause instability. If the reagent of choice is sodium bisulfite, temperatures above about 150° C. and pH above about 10 should be avoided in order to prevent decomposition of the bisulfite adduct, which could lead to undesirable sulfur impurities in the ethylene oxide or ethylene glycol products of the manufacturing process. Since sodium bisulfite is capable of rapid reaction with formaldehyde even at low concentrations, e.g., about 100 parts per million of formaldehyde, it is possible to introduce the bisulfite successfully into aqueous process streams containing quite dilute solutions of formaldehyde. In order to avoid introducing sulfur impurities into the organics in the process (e.g., ethylene glycol), it is desirable to introduce and maintain the bisulfite in the aqueous side of the process.

Although the method of the invention has thus far been described primarily in terms of an ethylene oxide/glycol process with a bisulfite as the reagent of choice, it will be readily appreciated that other reagents could also be used in an ethylene/glycol process, and that the method of the invention could also be applied to other processes.

In another variation on the present method, aldehydes, and particularly formaldehyde, can be removed by treatment of the process stream with a reagent which forms a precipitate with the aldehyde. One such reagent is dinitrophenylhydrazine. It will be apparent, however, that the presence of a precipitate presents certain handling problems, which must be accomodated through appropriate engineering to effect the separation of the solids.

In yet another variation on the present method, instead of introducing the reagent to the process stream, the process stream may be introduced to the reagent. Such a system could involve use of a bed of solid resin support to which the reagent is chemically bonded. For example, those common ion exchange resins known as Amberlite ® and Amberlyst ® (available from Rohm and Haas) are weakly basic and can be reacted with a bisulfite salt in aqueous solution to bind the bisulfite ion to the support. When an aldehyde-bearing process stream is passed over such a resin bed, the aldehyde will react with the bisulfite ion and will be retained on the resin, thereby purifying the stream of the aldehyde. The resin bed can thereafter be regenerated by washing with a basic solution to release the bound aldehyde.

EXAMPLES

Example 1

In order to evaluate the performance of various potential reagents on formaldehyde, the materials shown in Table I were screened.

TABLE 1

| Reagent name | Formula |
| --- | --- |
| Sodium Bisulfite | $NaHSO_3$ |
| Hydrogen Peroxide | $H_2O_2$ |
| Potassium Permanganate | $KMnO_4$ |
| Sodium Hypochlorite | $NaOCl$ |
| Ammonium Hydroxide | $NH_4OH$ |

These reagents were each mixed with a solution of 177 ppm formaldehyde in water, pH 6.4, 25° C. Only three reduced the amount of formaldehyde: sodium bisulfite, hydrogen peroxide, and potassium permanganate, with reductions of 99%, 27%, and 41%, respectively.

Example 2

A sample of water from an ethylene oxide manufacturing process stream, containing about 200 ppm formaldehyde, as well as smaller quantities of ethylene oxide, acetaldehyde, glycolaldehyde, and various other organic impurities not relevant to the present invention, was treated with 1.3 equivalents of sodium bisulfite under the same conditions as those used in Example 1. The amount of free formaldehyde was reduced to less than 1 ppm; surprisingly, however, the amounts of the other aldehydes and the ethylene oxide remained essentially unchanged. This demonstrates that sodium bisulfite reacts preferentially with formaldehyde, thereby minimizing the amount of that reagent required to effect the purification, and does not reduce the ethylene oxide efficiency of the manufacturing process. The product of the reaction was the adduct, hydroxymethanesulfonic-acid monosodium salt, a non-volatile, water-soluble material. The results of these experiments showed that formaldehyde can be converted into a nonvolatile salt under conditions typical of those encountered in ethylene oxide manufacturing. By application of this method at any appropriate point upstream of the ethylene oxide recovery still, the quality of the ethylene oxide distilled from the recovery still will be significantly improved. There will also be a corresponding improvement in the quality of ethylene glycol, as the amount of UV absorbers formed will also be reduced.

Example 3

A commercial aqueous process stream, typical of the tails from the primary water absorber shown in the Kirk-Othmer article referenced above, was treated according to the method of the invention. The stream contained approximately 4–6% by weight ethylene oxide, several thousand parts per million ethylene glycol, and about 100 ppm formaldehyde, as well as smaller amounts of acetaldehyde and glycolaldehyde, and varied in pH from about 5–8, and in temperature from about 35°–100° C.. The stream was continuously treated under ambient conditions by introducing to it a 38 weight percent aqueous solution of sodium bisulfite at a formaldehyde: bisulfite equivalent ratio of about 4.5. The formaldehyde concentration in the stream dropped to less than 5 ppm after only a few hours. A similar reduction in formaldehyde occurred in all streams downstream of the treated stream. The concentrations of the ethylene oxide, ethylene glycol, and the other aldehydes were unchanged by the treatment. Build-up of the sodium salt reaction product was controlled by removing a purge stream, from which the ethylene glycol also could be removed. The remainder of the treated stream was recycled to the main process.

Example 4

The method of Example 3 was repeated, except that an equivalent ratio of about 2.5 was used. Similar beneficial results were obtained; however, more time was required to realize the greatest reduction in formaldehyde content.

We claim:

1. A method for removing a reactive, relatively volatile, impurity or by-product in a process from an aqueous process stream in which such impurity is dissolved, comprising:
   (a) applying to said aqueous process stream a water-soluble reactant under conditions under which said reactant reacts with said impurity or by-product to form in aqueous solution a reaction product or products having a lower volatility than said impurity or by-product, and
   (b) removing at least a portion of said reaction product or products from the process.

2. A method of claim 1 wherein said impurity is an aldehyde.

3. A method of claim 2 wherein said impurity is formaldehyde.

4. A method of claim 2 wherein said impurity is acetaldehyde.

5. A method of claim 1 wherein said impurity is an inorganic impurity.

6. A method of claim 1 wherein said reactant is an oxidizing or reducing agent.

7. A method of claim 6 wherein said reducing agent is an inorganic salt.

8. A method of claim 7 wherein said inorganic salt is an alkali metal or ammonium sulfite or bisulfite.

9. In a process for making an alkylene oxide by the catalytic epoxidation of the corresponding alkene, a method for separating aldehyde by-product from at least some higher molecular weight aldehyde by-products and from the alkylene oxide in a process stream in which they are dissolved in water, comprising:
   (a) mixing with said aqueous process stream a water-soluble reactant which preferentially reacts with formaldehyde, before other aldehydes that may be present, under the conditions of the process stream to form in aqueous solution a reaction product having lower volatility than formaldehyde, and
   (b) removing at least a portion of said reaction product from the process.

10. A method of claim 9 wherein the reactant also reacts with an aldehyde other than formaldehyde.

11. A method of claim 9 wherein said reactant is an oxidizing or reducing agent.

12. A method of claim 11 wherein said reducing agent is an inorganic salt.

13. A method of claim 12 wherein said inorganic salt is an alkali metal or ammonium sulfite or bisulfite.

14. A method of claim 9 further comprising reaction of the reactant with $NO_x$.

15. In a process for making alkylene oxide by the reaction of alkene and oxygen in which a stream containing alkene, oxygen, gas-phase inhibitor and at least one efficiency-enhancing gaseous member of a redox-half reaction pair is fed under alkylene oxide-producing conditions to a bed of catalyst comprising an impregnated silver metal on an inert, refractory solid support and an efficiency-enhancing amount of at least one efficiency-enhancing salt of a member of a redox-half reaction pair, a method for separating aldehyde by-product from higher molecular weight aldehyde by-products and from the alkylene oxide in a process stream in which they are dissolved in water, comprising:
   (a) mixing with said aqueous process stream a water-soluble reactant which preferentially reacts with formaldehyde, before other aldehydes that may be present, under the ambient conditions of the process stream to form in aqueous solution a reaction product having lower volatility than formaldehyde, and
   (b) removing at least a portion of said reaction product from the process.

16. A method of claim 15 wherein said reactant is an oxidizing or reducing agent.

17. A method of claim 16 wherein said reducing agent is an inorganic salt.

18. A method of claim 17 wherein said inorganic salt is an alkali metal or ammonium sulfite or bisulfite.

19. A method of claim 15 wherein at least one gaseous member of a redox-half reaction is NO, $NO_2$, $N_2O_3$, $N_2O_4$, or a gas capable of forming one of the aforementioned gases under the conditions of the process.

20. A method of claim 15 wherein the reactant also reacts with aldehyde other than formaldehyde.

* * * * *